(12) United States Patent
Jamous et al.

(10) Patent No.: US 10,413,709 B2
(45) Date of Patent: Sep. 17, 2019

(54) HIGH-PRESSURE DILATATION CATHETER BALLOON

(71) Applicant: Medtronic Vascular, Inc., Santa Rosa, CA (US)

(72) Inventors: Aram Jamous, Ballybrit (IE); Colm Connolly, Ballybrit (IE); Colin Meade, Ballybrit (IE); Niall Plunkett, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 440 days.

(21) Appl. No.: 15/209,874

(22) Filed: Jul. 14, 2016

(65) Prior Publication Data

US 2018/0015265 A1 Jan. 18, 2018

(51) Int. Cl.
*A61M 25/10* (2013.01)
*B29C 53/02* (2006.01)
(Continued)

(52) U.S. Cl.
CPC ...... *A61M 25/104* (2013.01); *A61M 25/1011* (2013.01); *A61M 25/1029* (2013.01);
(Continued)

(58) Field of Classification Search
CPC ...... A61M 25/1011; A61M 2025/1077; A61M 2025/1013; A61M 25/1029;
(Continued)

(56) References Cited

U.S. PATENT DOCUMENTS 3,173,418 A * 3/1965 Baran .................. A61M 16/04
128/207.15
4,608,984 A * 9/1986 Fogarty ............... A61M 25/104
604/913
(Continued)

FOREIGN PATENT DOCUMENTS

EP 0582870 A2 2/1994

OTHER PUBLICATIONS

PCT/US2017/037037, The International Search Report and the Written Opinion of the International Searching Authority, dated Sep. 6, 2017, 14pgs.

*Primary Examiner* — Kathleen S Holwerda
(74) *Attorney, Agent, or Firm* — Medler Ferro Woodhouse & Mills PLLC (57) ABSTRACT

A dilatation catheter includes a high-pressure balloon component comprising an inner balloon and an outer balloon. An interior of the inner balloon is in fluid communication with a lumen of the catheter for receiving inflation fluid therefrom. The outer balloon defines a separate interior within which the inner balloon is disposed. The outer balloon has a hole in a wall thereof for venting the interior of the outer balloon to ambient environment. Proximal necks of the inner and outer balloons are bonded to an outer shaft of the catheter and distal necks of the inner and outer balloons are bonded to an inner shaft of the catheter. In accordance with embodiments hereof, the interior of the outer balloon is not in fluid communication with the interior of the inner balloon, the lumen of the catheter or any other source of fluid from the catheter.

15 Claims, 7 Drawing Sheets

(51) Int. Cl.
    *B29C 65/08*     (2006.01)
    *B29C 65/16*     (2006.01)
    *B29C 65/48*     (2006.01)
    *B29C 65/00*     (2006.01)
    *B29L 31/00*     (2006.01)

(52) U.S. Cl.
    CPC ......... *A61M 25/1034* (2013.01); *B29C 53/02* (2013.01); *B29C 65/08* (2013.01); *B29C 65/16* (2013.01); *B29C 65/48* (2013.01); *B29C 66/534* (2013.01); *A61M 2025/1004* (2013.01); *A61M 2025/1013* (2013.01); *A61M 2025/1077* (2013.01); *B29L 2031/7543* (2013.01)

(58) Field of Classification Search
    CPC ............ A61M 25/1034; A61M 25/104; A61M 16/0456; A61B 2025/1004; A61F 2/958; B29C 53/02; B29C 65/08; B29C 65/16; B29C 65/48
    See application file for complete search history.

(56) References Cited

U.S. PATENT DOCUMENTS

| | | | |
|---|---|---|---|
| 4,811,737 A | | 3/1989 | Rydell |
| 5,728,065 A | | 3/1998 | Follmer et al. |
| 6,242,063 B1 | * | 6/2001 | Ferrera ................. A61L 29/049 |
| | | | 428/35.2 |
| 8,827,953 B2 | * | 9/2014 | Rocha-Singh .......... A61F 2/945 |
| | | | 604/101.02 |
| 2008/0140001 A1 | | 6/2008 | Globerman et al. |
| 2011/0130719 A1 | * | 6/2011 | Aggerholm ............. A61F 2/958 |
| | | | 604/101.02 |

\* cited by examiner

HIGH-PRESSURE DILATATION CATHETER BALLOON

FIELD OF THE INVENTION

In general, the invention relates to balloon catheters and more particularly, the invention relates to a dilatation catheter balloon having nested inner and outer balloons that achieve a combination of high burst strength, low deflated profile, low diameter compliance and good trackability.

BACKGROUND OF THE INVENTION

Cardiovascular disease, including atherosclerosis, is a leading cause of death globally. Atherosclerosis is a slow, progressive disease for which an exact cause is unknown. It is believed however that atherosclerosis may start with damage or injury to an inner layer of an artery, with such damage possibly being caused by: high blood pressure, high cholesterol, high triglycerides (a type of fat (lipid) in the blood), smoking and other sources of tobacco, insulin resistance, obesity or diabetes, inflammation from diseases (such as arthritis, lupus or infections), and/or inflammation of unknown cause. Once the inner wall of an artery is damaged, blood cells and other substances often attack the injury site and build up in the inner lining of the artery. Over time, fatty deposits or plaques made of cholesterol and other cellular products also build up at the injury site and harden into calcified lesions, thereby narrowing the affected arteries.

One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery. Conventionally, angioplasty may be accomplished by inflating a dilatation balloon of a balloon or angioplasty catheter within the narrowed lumen of the artery to dilate the vessel by controlled stretching and tearing of the vessel wall and, to a certain extent, compressing soft plaque against the vessel wall. Inflation of the balloon is accomplished by supplying a pressurized fluid through an inflation lumen of the catheter which is connected to an inflation apparatus located outside of the patient's body. Similarly, applying suction to the inflation lumen collapses the balloon to its minimum dimension or low profile for initial placement of the balloon catheter within or removal from the target blood vessel.

Figure 1A:
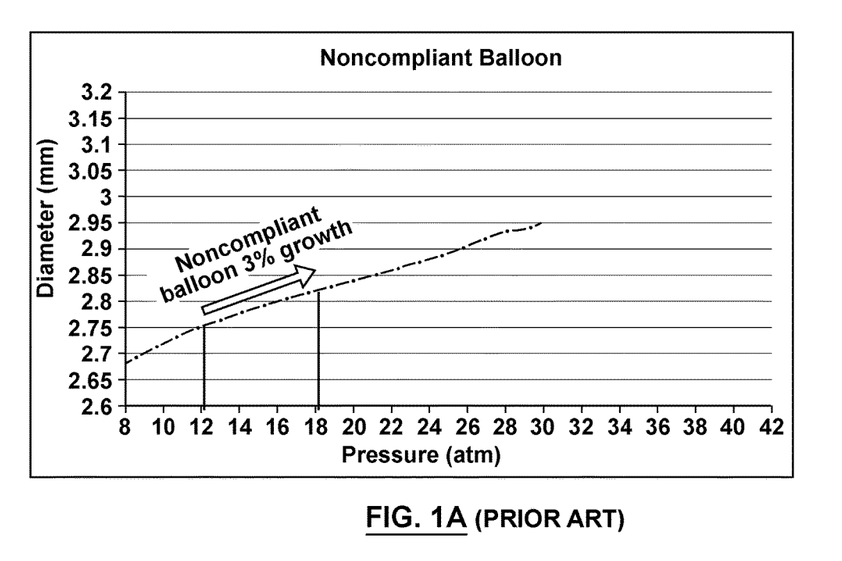
FIG. 1A is a graph that depicts a diameter compliance curve for a noncompliant balloon.
Figure 1B:
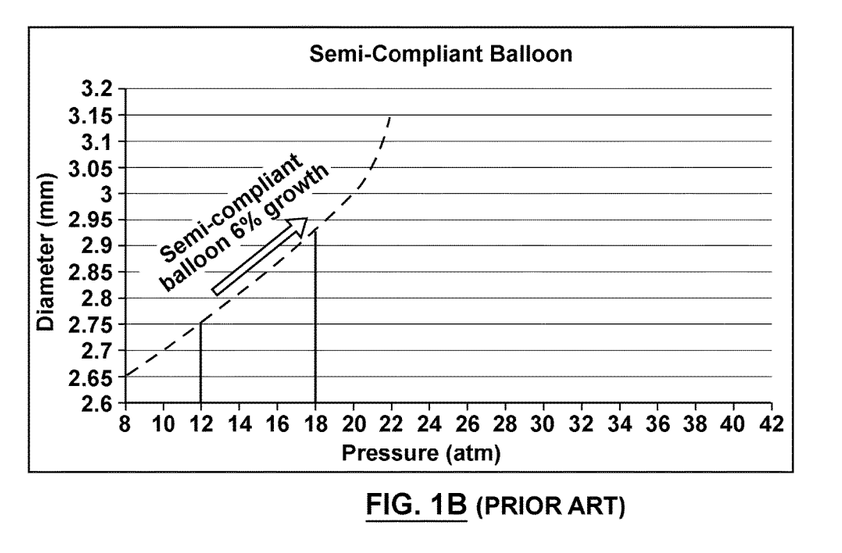
FIG. 1B is a graph that depicts a diameter compliance curve for a semi-compliant balloon.

A variety of angioplasty catheter designs and constructions are available. Typically, a dilatation balloon of an angioplasty catheter is constructed and configured to produce a nominal or preferred/rated inflated diameter at a specified inflation pressure, with standard inflation pressures being between two and twenty atmospheres (30 Psi to approximately 300 Psi). Medical dilatation balloons may be classified as being compliant, noncompliant or semi-compliant depending on the increase in diameter of the balloon under increasing inflation pressure. A compliant balloon is characterized by continued expansion as internal pressure increases. For instance, a compliant balloon will continue to radially expand beyond its preferred or rated inflated diameter in response to increasing inflation pressure. A noncompliant balloon is characterized by little growth of the balloon's preferred or rated inflated diameter over a range of customary inflation pressures, such as 3% growth in the nominal inflated diameter between 12 Atm and 18 Atm, as shown by the diameter compliance curve of the graph illustrated in FIG. 1A. A noncompliant balloon will have a maximum diameter growth percentage as low as is possible, typically not more than 5%. A semi-compliant balloon is one that provides, over a range of customary inflation pressures, a lesser degree of radial expansion beyond its nominal inflated diameter than a compliant balloon, such as 6% growth in the nominal inflated diameter between 12 Atm and 18 Atm, as shown by the diameter compliance curve of the graph illustrated in FIG. 1B. Typically, the radial expansion of a semi-compliant balloon is from 6 to 10%. The graphs of FIGS. 1A and 1B are based on the performance of known noncompliant and semi-compliant dilatation balloons having equivalent dimensions and wall thicknesses. The first non-compliant angioplasty balloon was invented by Stanley Levy and is described in U.S. Pat. No. RE32,983. The Levy patent describes a balloon reaching nominal, wrinkle-free diameter at 75-100 psi. Levy also teaches balloons having radial expansion beyond a nominal inflated diameter of less than 5% at 200 psi, or optionally less than 10% at 400 psi or 500 psi.

Figures 1C, 2:
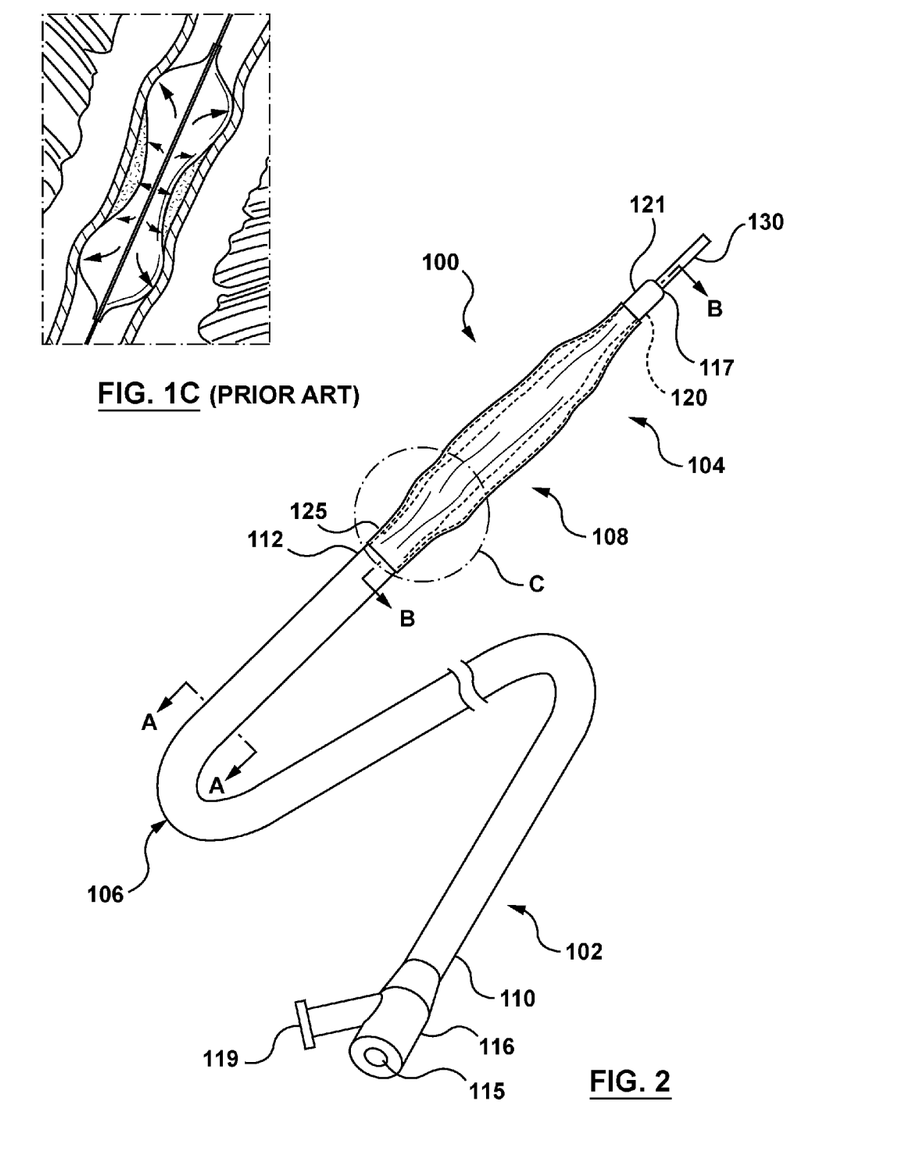
FIG. 1C is a depiction of a conventional dilatation balloon constrained in a dog-bone shape by a heavily calcified lesion of a vessel.
FIG. 2 is a perspective side view of a catheter in accordance with an embodiment hereof, with a high-pressure balloon component of the catheter in an uninflated or unexpanded configuration.

When used in a heavily calcified lesion a standard angioplasty balloon may not sufficiently disrupt the lesion but instead may "dog bone" as shown in FIG. 1C. "Dog bone" is a term of art meaning that a midsection of the balloon is prevented from expanding to its nominal inflated diameter by the hard calcification, whereas end sections of the balloon not constrained by the calcification inflate more than the midsection creating the so-called "dog bone" inflated shape. In such situations, balloon angioplasty with a standard dilatation balloon may not be effective in opening the stenosis, and the affected artery may still have a narrowing that requires a second angioplasty, or even a different treatment to be performed. One reason a standard balloon may "dog bone" is that it cannot exert enough radial force on a heavily calcified lesion before it exceeds its burst strength and fails.

Thus, it may be desirable during certain angioplasty procedures to utilize an angioplasty balloon with a higher rated burst pressure (RBP) than a conventional angioplasty balloon. It is known that increasing the wall thickness of a dilation balloon using the same material can achieve a relatively higher RBP than a standard balloon. However, the thicker-walled dilatation balloon thus-created can be expected to have drawbacks such as a larger deflated delivery profile and greater bending stiffness, e.g. reduced flexibility, a.k.a trackability, which in some circumstances may prohibit or impede navigation to, insertion within, and removal from a stenosed treatment site. As well due to processing of dilatation balloons that is necessary for beneficially orienting a material thereof, balloon walls of a certain thickness may develop a stress gradient between inner and outer surfaces of a "thicker walled" balloon that actually may inhibit the balloon from achieving higher burst strength. Thus there remains a need in the art for a high-pressure dilatation balloon for use in an angioplasty procedure that has a higher RBP such that it can be inflated to a sufficiently high pressure to break-up or compress even a heavily calcified lesion within a vessel. Such a balloon would beneficially have a noncompliant nature to avoid the "dog bone" effect and thereby dilate the resistant stenosis without over-stretching adjacent artery tissue. Further it would be advantageous for such a high-pressure angioplasty balloon to have a low profile and good trackability for navigation to and insertion within a calcified treatment site.

BRIEF SUMMARY OF THE INVENTION

A balloon catheter is disclosed that includes a high-pressure balloon component. The high-pressure balloon component includes an inner balloon that has proximal and distal neck segments, proximal and distal cone segments and a cylindrical body, and that defines an interior that is in fluid communication with a lumen of the catheter for receiving inflation fluid therefrom. The high-pressure balloon component also includes an outer balloon disposed about the inner balloon, the outer balloon having proximal and distal neck segments, proximal and distal cone segments and a cylindrical body. The outer balloon defines an interior within which the inner balloon is disposed, and the outer balloon has a hole in a wall thereof for venting the interior of the outer balloon to ambient environment. In order to form the balloon component and attach it to the remainder of the catheter, the proximal neck segments of the inner and outer balloons are bonded to an outer shaft component of the catheter and the distal neck segments of the inner and outer balloons are bonded to an inner shaft component of the catheter. The aforementioned hole in the wall of the outer balloon is formed within a non-bonded area of one of the proximal and distal neck segments of the outer balloon. In accordance with embodiments hereof, the interior of the outer balloon is not in fluid communication with the interior of the inner balloon, the lumen of the catheter or any other source of fluid from the catheter.

A balloon catheter is disclosed that includes a high-pressure balloon component. The balloon component includes an inner balloon having proximal and distal neck segments, proximal and distal cone segments and a cylindrical body, the inner balloon defining an interior that is in fluid communication with a lumen of the catheter for receiving inflation fluid therefrom. The balloon component also includes an outer balloon surrounding the inner balloon, the outer balloon having proximal and distal neck segments, proximal and distal cone segments and a cylindrical body. The outer balloon defines an interior within which the inner balloon is disposed, wherein the outer balloon has a hole in a wall thereof for venting the interior of the outer balloon to ambient environment. The hole is formed in the wall of the outer balloon in one of the proximal neck segment, the distal neck segment, the proximal cone segment and the distal cone segment. In order to form the balloon component and attach it to the remainder of the catheter, the proximal neck segments of the inner and outer balloons are bonded to an outer shaft component of the catheter, and the distal neck segments of the inner and outer balloons are bonded to an inner shaft component of the catheter.

A method of forming a balloon catheter is disclosed. The method includes possessing or utilizing first and second balloons to create a balloon component. Initially, the method provides for forming a hole in a wall of the second balloon in one of a proximal neck segment, a distal neck segment, a proximal cone segment and a distal cone segment of the second balloon. The method includes folding the first balloon and pulling the folded first balloon within the second balloon, so as to coaxially align proximal neck segments of the first and second balloons. Thereafter, the method includes forming a proximal bond to attach the proximal neck segments of the first and second balloons to an outer shaft component. The method also includes coaxially aligning distal neck segments of the first and second balloons, and thereafter forming a distal bond to attach the distal neck segments of the first and second balloons to an inner shaft component. In a method of forming a balloon catheter in accordance herewith, an interior of the first balloon is configured to be in fluid communication with a lumen of the balloon catheter for receiving inflation fluid therefrom, the first balloon is disposed within an interior of the second balloon, and the interior of the second balloon is not configured to be in fluid communication with the interior of the first balloon, the lumen of the balloon catheter or any other source of fluid from the catheter. In an embodiment of the method, the step of forming a hole in a wall of the second balloon includes forming the hole in one of a proximal neck segment and a distal neck segment, and the step of forming a bond includes not bonding an area of one of the proximal and distal neck segments of the second balloon that includes the hole.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, renal and other peripheral arteries, the invention may also be used in any other body passageways where it is deemed useful. Furthermore, there is no intention to be bound by any expressed or implied theory presented in the preceding technical field, background, brief summary or the following detailed description.

Figure 2A:
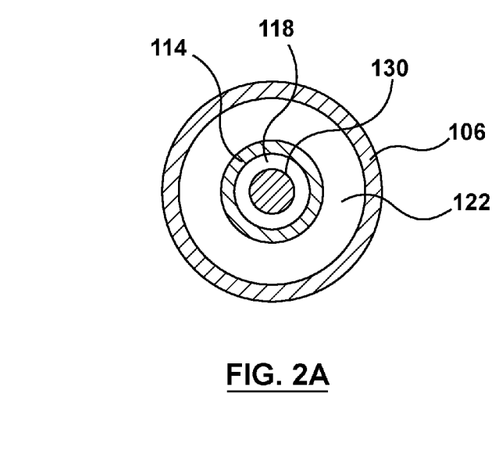
FIG. 2A is a cross-sectional view taken along line A-A of FIG. 2 in accordance with an embodiment hereof.

FIGS. 2 and 2A depict a balloon catheter 100 in accordance with an embodiment hereof. The catheter 100 includes a proximal segment 102 having a hub 116 that is accessible by a clinician outside of a patient and a distal segment 104 having a high-pressure dilatation balloon component 108 that is positionable at a treatment site within the vasculature. The balloon component 108 is shown in an uninflated or unexpanded configuration in FIG. 2 and in an expanded or inflated configuration in FIG. 3B. In embodiments hereof, the catheter 100 may be used in balloon angioplasty procedures, as well as may form the basis of a stent delivery system, and/or a graft delivery system.

The catheter 100 includes an elongate tubular or outer shaft component 106 having a proximal end 110 coupled to the hub 116 and a distal end 112 coupled to the balloon component 108. In the embodiment shown in FIGS. 2 and 2A, by way of example and not limitation, the catheter 100 has an over-the-wire (OTW) configuration with an inner shaft component 114 extending through each of the outer shaft component 106 and the balloon component 108. Inner shaft component 114 defines a lumen 118 therethrough for accommodating a guidewire 130. In another embodiment, the catheter 100 may be modified to have a rapid exchange (RX) configuration without departing from the scope hereof such that an inner shaft component extends within only the distal segment 104 of the catheter 100. In the present embodiment shown in FIGS. 2 and 2A, the inner shaft component 114 has a proximal end (not shown) coupled to a proximal port 115 of the hub 116 and a distal end 120 terminating distally of the balloon component 108. In an embodiment, the distal end 120 of the inner shaft component 114 may form at least a portion of an atraumatic distal tip 121 of the catheter 100 that defines a distal port 117 of the lumen 118. In another embodiment a separate atraumatic distal tip component may be coupled to the distal end of the catheter 100 without departing from the scope hereof, as would be understood by one of ordinary skill in the art of catheter design.

In the coaxial catheter construction depicted in the present embodiment, the inner shaft component 114 extends within the outer shaft component 106 such that a substantially annular lumen 122 is defined therebetween for the length of the proximal segment 102 of the catheter 100. Other types of catheter construction are also suitable for embodiments hereof, such as by way of example and not limitation, a multi-lumen catheter shaft construction formed by extrusion. The annular lumen 122 extends between the proximal and distal ends 110, 112 of the outer shaft component 106 to allow inflation fluid received through an inflation port 119 of the hub 116 to be delivered to the balloon component 108, as explained in more detail below. As would be understood by one of ordinary skill in the art of catheter design, the hub 116 provides a Luer hub or other type of fitting that may be connected to a source of inflation fluid and may be of another construction or configuration than that depicted in FIG. 2 without departing from the scope hereof.

Figure 2B:
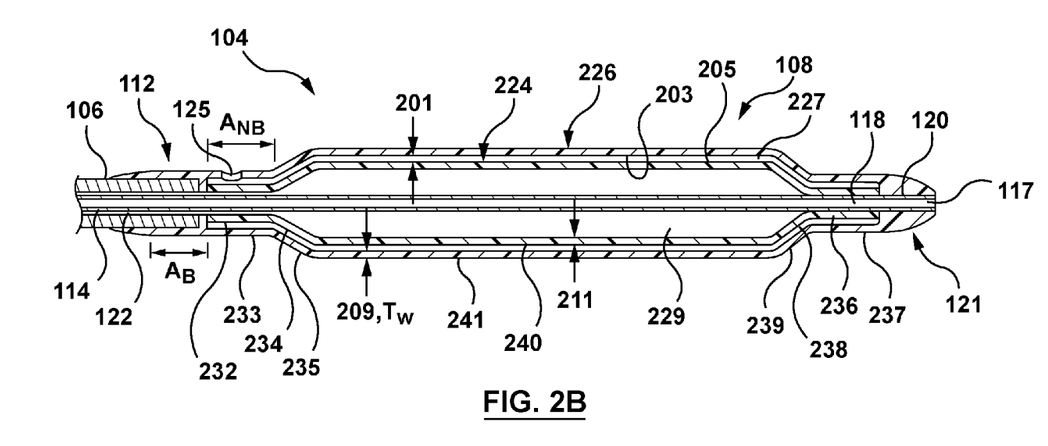
FIG. 2B is a sectional view of a distal segment of the catheter of FIG. 2 taken along line B-B thereof in accordance with an embodiment hereof.

FIG. 2B is a longitudinal sectional view of the distal segment 104 of the catheter 100 taken along line B-B of FIG. 2 with the guidewire 130 omitted for ease of illustration. The high-pressure balloon component 108 of the distal segment 104 includes an inner balloon 224 and an outer balloon 226. The outer balloon 226 surrounds the inner balloon 224 such that the inner balloon 224 may be described as being disposed within an interior 227 defined by the outer balloon 226. The inner balloon 224 defines an interior 229 that is in fluid communication with the annular lumen 122 of the proximal segment 102 of the catheter 100 for receiving inflation fluid therefrom when inflation of the inner balloon 224 and thereby inflation of the balloon component 108 are desired. Conversely, the interior 227 of the outer balloon 226 is not in fluid communication with the annular lumen 122 of the proximal segment 102, the interior 229 of the inner balloon 224, or any other source of fluid from the catheter 100. Accordingly, the interior 227 of the outer balloon 226 does not receive inflation fluid therein but instead the outer balloon 226 is expanded by the inflation of the inner balloon 224 as described below.

The inner balloon 224 of the balloon component 108 is a tubular structure of a suitable dilatation balloon material that is formed to define a proximal neck segment 232, a tapered proximal cone segment 234, a distal neck segment 236, and a tapered distal cone segment 238, with a working or cylindrical body segment 240 extending between the proximal cone segment 234 and the distal cone segment 238. Similarly, the outer balloon 226 of the balloon component 108 is a tubular structure of a suitable dilatation balloon material that is formed to define a proximal neck segment 233, a tapered proximal cone segment 235, a distal neck segment 237, and a tapered distal cone segment 239, with a working or cylindrical body segment 241 extending between the proximal cone segment 235 and the distal cone segment 239. Each of the proximal cone segments 234, 235 is frustoconical in shape and tapered proximally, such that a narrow proximal end of the respective cone segment 234, 235 is adjacent to its respective proximal neck segment 232, 233 and a wide distal end of the respective cone segment 234, 235 is adjacent to a proximal end of its respective cylindrical wall segment 240, 241. Similarly, each of the distal cone segments 237, 238 is frustoconical in shape and tapered distally, such that a wide proximal end of the respective cone segment 237, 238 is adjacent to a distal end of its respective cylindrical wall segment 240, 241 and a narrow distal end of the respective cone segment 237, 238 is adjacent its respective distal neck segment 236, 237.

The proximal neck segments 232, 233 of the inner and outer balloons 224, 226 are joined or bonded to the distal end 112 of the outer shaft component 106 and the distal neck segments 236, 237 of the inner and outer balloons 224, 226 are joined or bonded to the distal end 120 of the inner shaft component 114. In an embodiment hereof, the proximal and distal neck segments of the inner and outer balloons 224, 226 may be thermally bonded or melt bonded to the outer shaft component 106 and the inner shaft component 114, respectively. In embodiments hereof, thermal or melt bonding of the components may be achieved by any conventional manner known to one of skill in the art of balloon catheter construction, such as by one or more of laser welding, heat fusing, and/or ultrasonic welding. In other embodiments in addition or as an alternative to thermal or melt bonding, suitable adhesives may be used for joining the inner and outer balloons 224, 226 to the outer shaft component 106 and the inner shaft component 114, as would be known to one of skill in the art of balloon catheter construction.

In the embodiment shown in FIGS. 2 and 2B, the joined, bonded, and/or melted portion of the distal end 120 of the inner shaft component 114 in combination with joined, bonded, and/or melted distalmost portions of the distal neck segments 236, 237 of the inner and outer balloons 224, 226 form the atraumatic distal tip 121 of the catheter 100 and define the distal port 117 of the lumen 118. Alternatively, as previously stated above, a separate atraumatic distal tip component may be coupled to the distal end of the catheter 100, as would be understood by one of ordinary skill in the art of catheter design without departing from the scope hereof.

Figure 2C:
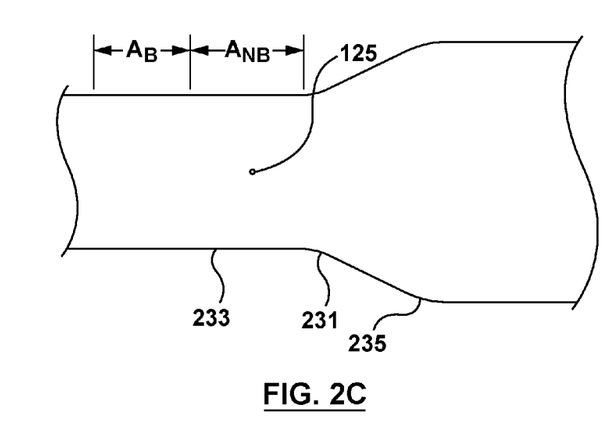
FIG. 2C is an enlarged top view of a proximal junction area C of the balloon component shown in FIG. 2 in accordance with an embodiment hereof.

FIG. 2C is an enlarged top view of a proximal junction area C of the balloon component 108. With reference to FIGS. 2, 2B and 2C, a hole or aperture 125 is shown formed through a wall 209 of the outer balloon 226 within the proximal neck segment 233. Although the hole 125 is illustrated in FIGS. 2 and 2B (and in subsequent FIGS. 3A, 3B, and 4A-4D) as being somewhat substantial, this is for illustrative purposes only as a hole 125 in accordance with embodiments hereof is instead essentially a pinhole of an extremely small diameter. A size of a hole 125 is better represented in FIG. 2C, as the hole 125 is shown in relationship to a remainder of the proximal neck segment 233 of the outer balloon 226. In embodiments hereof, a diameter of a hole 125 may be approximately 0.005 inch.

The hole 125 is a vent provided through the wall 209 of the outer balloon 226 in order to ensure when the inner balloon 224 is pressurized that it will make complete contact with the outer balloon 226, as the hole 125 permits any air or other fluid between the two balloons to be expelled during at least an initial inflation as described below. In embodiments hereof, providing the hole 125 in an area of the wall 209 having low biaxial polymer orientation, such as in a proximal or distal cone or neck segment, does not impede the balloon component's improved burst capability and provides the benefits of reducing or prohibiting localized pressure differentials from occurring in the balloon component 108 that could lead to burst variation and/or difficulty in wrapping the balloon component 108 into a low profile. The hole 125 in the outer balloon 226 is the only point of ingress and egress, i.e., fluid communication, between the interior 227 of the outer balloon 226 and the external environment and, as stated above, the outer balloon 226 has no further openings or apertures and interior 227 has no other fluid communication with either of the external environment or any other component(s) of the catheter 100.

In the depicted embodiment, the hole 125 is located along the proximal neck segment 233 to be proximal of a juncture 231 of the outer balloon 226, wherein the juncture 231 is substantially a demarcation between the cylindrical proximal neck segment 233 and the tapered proximal cone segment 235 thereof. The hole 125 is located in a non-bonded area $A_{NB}$ of the proximal neck segment 233 so as to provide a vent or fluid pathway between the interior 227 of the outer balloon 226 and the ambient environment. Stated another way, the hole 125 is formed through the proximal neck segment 233 at a point or location that is distal of a proximal balloon bond or bonded area $A_B$, wherein the bond area $A_B$ is comprised of joined, bonded, and/or melted proximalmost portions of the proximal neck segments 232, 233 of the inner and outer balloons 224, 226 and a joined, bonded, and/or melted portion of the distal end 112 of the outer shaft component 106.

When the balloon component 108 is in an uninflated or unexpanded state, although not easily discernable in FIGS. 2 and 2B, a wall 211 of the inner balloon 224 is or may appear wrinkled at least along the cylindrical body segment 240 thereof. In the uninflated state shown in FIG. 2B, in addition to being wrinkled, the inner balloon 224 and the outer balloon 226 are shaped and sized such that a space or a gap 201 is defined or occurs therebetween within the interior 227 of the outer balloon 226. In an embodiment, by "space" or "gap" it is meant that an open area, volume or void exists within the interior 227 between at least a portion of an inner surface 203 of the outer balloon 226 and at least a portion of an outer surface 205 of the uninflated inner balloon 224. It should be understood that although FIG. 2B depicts the space 201 between the uninflated inner and outer balloons 224, 226 to be well-defined, such as to look like a uniform annular space for instance, this is by way of illustration only and the actual space 201 therebetween may appear amorphous or haphazard due to the wrinkled nature of the uninflated inner and outer balloons.

Figure 3A:
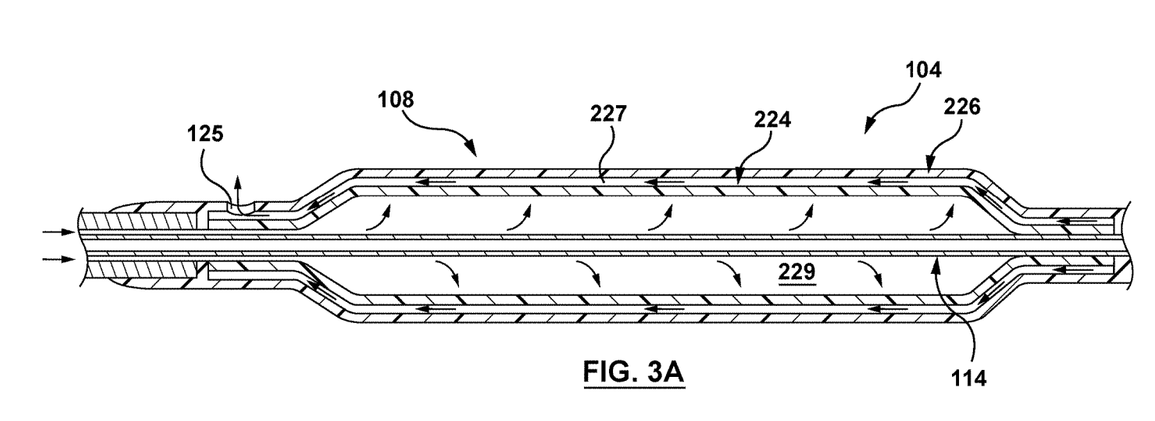
FIG. 3A is a longitudinal section of a portion of the distal segment of the catheter of FIG. 2 with the balloon component shown being inflated to an expanded configuration in accordance with an embodiment hereof.
Figure 3B:
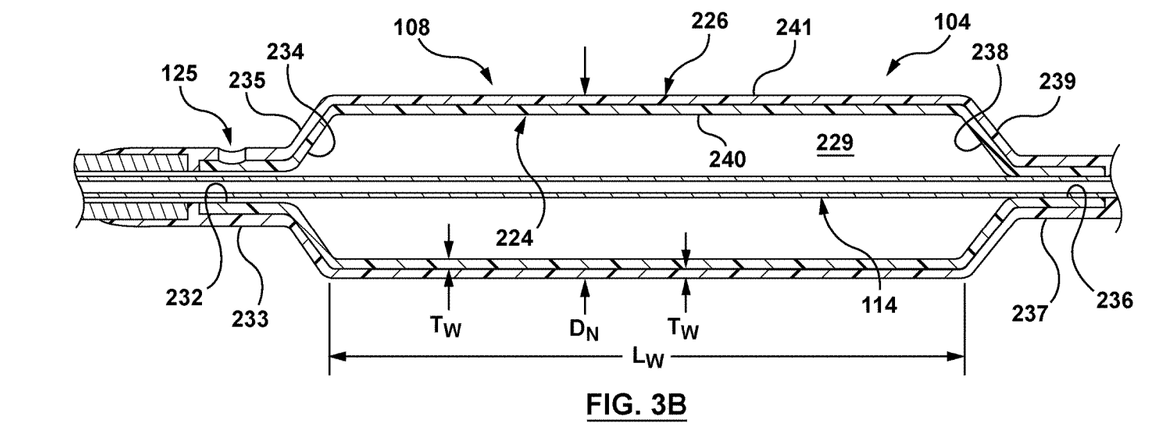
FIG. 3B depicts the balloon component of FIG. 3A in a fully expanded configuration in accordance with an embodiment hereof.

In accordance with an embodiment hereof, FIG. 3A is a longitudinal sectional view of a portion of the distal segment 104 of the catheter 100 of FIG. 2 with the balloon component 108 shown during inflation to a fully expanded configuration shown in FIG. 3B. When the inner balloon 224 receives inflation fluid, which is represented by arrows within the interior 229 of the inner balloon 224, the inner balloon 224 radially expands within the interior 227 of the outer balloon 226. During expansion of the inner balloon 224 within the interior 227 of the outer balloon 226, the inner balloon 224 expands to fill the space or gap between the inner and outer balloons 224, 226. During at least an initial expansion of the inner balloon 224 within the outer balloon 226, any residual air or fluid captured or remaining in the space or gap 201 of the interior 227 is forced out of or is expelled through the hole 125 in the outer balloon 226, which is represented by various arrows within the interior 227. In an embodiment "residual air" is meant to refer to air or other fluid that may get trapped during assembly of the balloon component 108 in the space or gap of the interior 227, with the space or gap being defined between the assembled inner and outer balloons 224, 226. In an embodiment during expansion of the inner balloon 224 by inflation fluid, the cylindrical wall 211 of the inner balloon 224 will become smooth and wrinkle-free. In an embodiment, the inner balloon 224 will achieve a smooth and wrinkle-free appearance at less than full pressurization of the balloon component 108. In an embodiment during expansion of the inner balloon 224 by inflation fluid, the inner balloon 224 will achieve a smooth and wrinkle-free appearance when pressurized to between 5 Atm and 8 Atm.

FIG. 3B depicts the balloon component 108 of FIG. 3A in a fully expanded configuration in accordance with an embodiment hereof, wherein the balloon component 108 is expanded to its nominal diameter $D_N$ and is pressurized at a high working pressure. In the expanded configuration, the expanded inner balloon 224 substantially fills the interior 227 of the outer balloon 226 and makes contact with an inner surface of the outer balloon 226. A benefit of the present design is that the inner and outer balloons 224, 226 beneficially interfere with each other and thereby contribute to the assembled balloon component 108 having a higher burst strength than either of the inner or outer balloons individually. In a test, prepared examples of a single balloon in accordance with the invention reached burst at an average of 24 Atm. However, when two of the exemplary balloons were assembled or nested together in accordance with the invention, the resulting average burst pressure was 40 Atm. Single-walled balloons having twice the wall thickness of the exemplary balloons, i.e. being as thick as the combined wall thickness of two balloons nested together, burst before reaching 40 Atm. The hole 125 will not adversely affect the burst strength of the balloon component 108 as the outer balloon 226 is not directly pressurized by any fluid but instead acts to provide a caging effect to the expanded and pressurized inner balloon 224. Stated another way when the balloon component 108 is in the fully expanded configuration, the outer balloon 226 tends to constrain further radial expansion of the inner balloon 224 thereby allowing a high pressure to be maintained by the balloon component 108 without bursting or rupturing. Together the nested inner and outer balloons 224, 226 enable the balloon component 108 to possess high burst strength. In an embodiment, the balloon component 108 may maintain a high working pressure of at least 35 Atm without bursting. In examples prepared according to the invention, burst pressures ranging from 35 Atm to 58 Atm were realized. Accordingly, a balloon component in accordance with embodiments hereof may be referred to as a high pressure dilatation balloon.

In an embodiment when the balloon component 108 is expanded and pressurized to a high working pressure, at least an outer surface of the cylindrical body segment 240 of the inner balloon 224 and an inner surface of the cylindrical body segment 241 of the outer balloon 226 are in continuous contact with each other such that the outer balloon 226 provides the caging effect noted above. In another embodiment when the balloon component 108 is expanded and pressurized to a high working pressure, outer surfaces of at least portions of the tapered proximal and distal cone segments 234, 238 of the inner balloon 224 and inner surfaces of at least portions of the tapered proximal and distal cone segments 235, 239 of the outer balloon 226, respectively, may also be in continuous contact with each other. In another embodiment when the balloon component 108 is expanded and pressurized to a high working pressure, outer surfaces of at least portions of the proximal and distal neck segments 232, 236 of the inner balloon 224 and inner surfaces of at least portions of the proximal and distal neck segments 233, 237 of the outer balloon 226, respectively, may also be in continuous contact with each other.

Figure 4A:
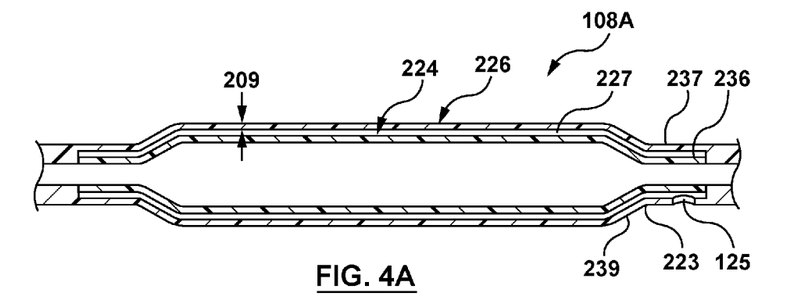
FIGS. 4A-4D are sectional views of various balloon components in accordance with embodiments hereof.

FIGS. 4A-4D are sectional views of balloon components 108A, 108B, 108C, 108D in accordance with embodiments hereof that depict various locations for a venting hole 125 or venting holes 125a, 125b. The balloon components 108A, 108B, 108C, 108D are shown separated from a remainder of the balloon catheter for ease of illustration. In the embodiment of FIG. 4A, a single hole or aperture 125 is shown formed through the wall 209 of the outer balloon 226 within the distal neck segment 237 to provide a vent or fluid pathway between the interior 227 of the outer balloon 226 and the ambient environment. In the embodiment depicted in FIG. 4A, the hole 125 is located along the distal neck segment 237 to be distal of a juncture 223 of the outer balloon 226, wherein the juncture 223 is substantially a demarcation between the cylindrical distal neck segment 237 and the tapered distal cone segment 239 thereof. As would be understood by the discussion above, the hole 125 is located in a non-bonded area of the distal neck segment 237 and therefore would be formed through the distal neck segment 237 at a point or location that is proximal of a distal balloon bond or bonded area comprised of joined, bonded, and/or melted distalmost portions of the distal neck segments 236, 237 of the inner and outer balloons 224, 226 and a joined, bonded, and/or melted portion of the distal end 121 of the inner shaft component 114 (not shown in FIG. 4A).

Figure 4B:
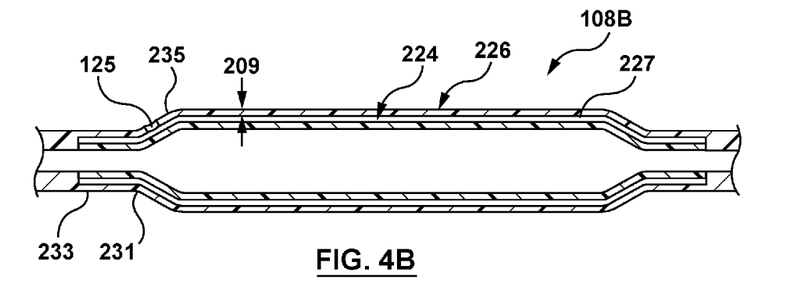
Figure 4C:
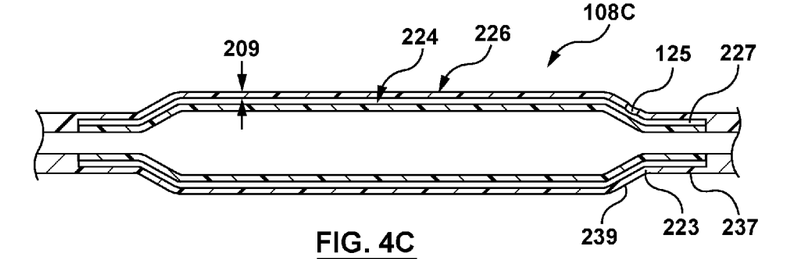
Figure 4D:
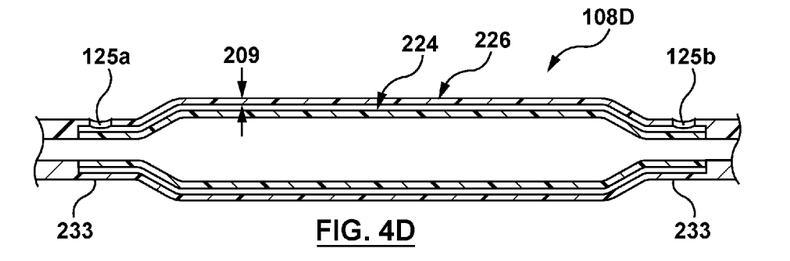

In the embodiment of FIG. 4B, a single hole or aperture 125 is shown formed through the wall 209 of the outer balloon 226 within the tapered proximal cone segment 235 to provide a vent or fluid pathway between the interior 227 of the outer balloon 226 and the ambient environment. In the embodiment depicted in FIG. 4B, the hole 125 is located along the narrow proximal end of the proximal cone segment 235 to be slightly or minimally distal of, or substantially proximate or adjacent to, the juncture 231 of the outer balloon 226. In the embodiment of FIG. 4C, a single hole or aperture 125 is shown formed through the wall 209 of the outer balloon 226 within the tapered distal cone segment 239 to provide a vent or fluid pathway between the interior 227 of the outer balloon 226 and the ambient environment. In the embodiment depicted in FIG. 4C, the hole 125 is located along the narrow distal end of the distal cone segment 239 to be slightly or minimally proximal of, or substantially proximate or adjacent to, the juncture 223 of the outer balloon 226. In the embodiment of FIG. 4D, a first hole 125a is shown formed through the wall 209 of the outer balloon 226 within a non-bonded area of the cylindrical proximal neck segment 233 and a second hole 125b is shown formed through the wall 209 of the outer balloon 226 within a non-bonded area of the cylindrical distal neck segment 237 to provide two vents or fluid pathways between the interior 227 of the outer balloon 226 and the ambient environment.

In embodiments hereof, each of the inner and outer balloons 224, 226 may be a semi-complaint angioplasty balloon formed from any suitable material for manufacture of an inflatable medical dilating balloon. Suitable materials for use in forming the inner and outer balloons 224, 226 include, by way of example and not limitation, polymers such as polyethylene, polyether block amide copolymer (PEBA), polyethylene terephthalate (PET), polyamide, polyurethane, and copolymers or blends thereof. Not all of the above listed materials are suitable for making semi-compliant balloons. The properties of the balloons may be enhanced by loading the balloon polymer with agents such as nanoclay, nanotubes, or graphene. In an embodiment, the inner and outer balloons 224, 226 may be of a polyether block amide copolymer that is known as PEBAX® 7033 SA 01 MED.

In an embodiment hereof and as described below, each of the inner and outer balloons 224, 226 of the balloon component 108 is of the same material and is molded such that at least the cylindrical body segments 240, 241 of the inner and outer balloons 224, 226, respectively, have the same wall thickness $T_W$, the same working length $L_W$, and the same rated or nominal inflated diameter $D_N$ (see FIG. 3B). For instance in an embodiment, by way of example and not limitation, each of the inner and outer balloons 224, 226 may be formed of PEBAX® 7033, and have a double wall thickness of approximately 0.0012 inch, a working length of 20 mm and a nominal inflated diameter $D_N$ of 2.75 mm. Note that, for efficiency and convenience, it is common industry practice to gently press deflated balloons flat and measure two wall thicknesses together, e.g. double wall thickness (DWT), with the understanding that the actual thickness of a single wall is half the measured DWT. Any difference in thickness of the two balloon walls measured together is typically negligible and can be disregarded. Thus, in the above embodiment, the measured DWT of 0.0012 inch relates to a single wall thickness of 0.0006 inch.

Figure 5A:
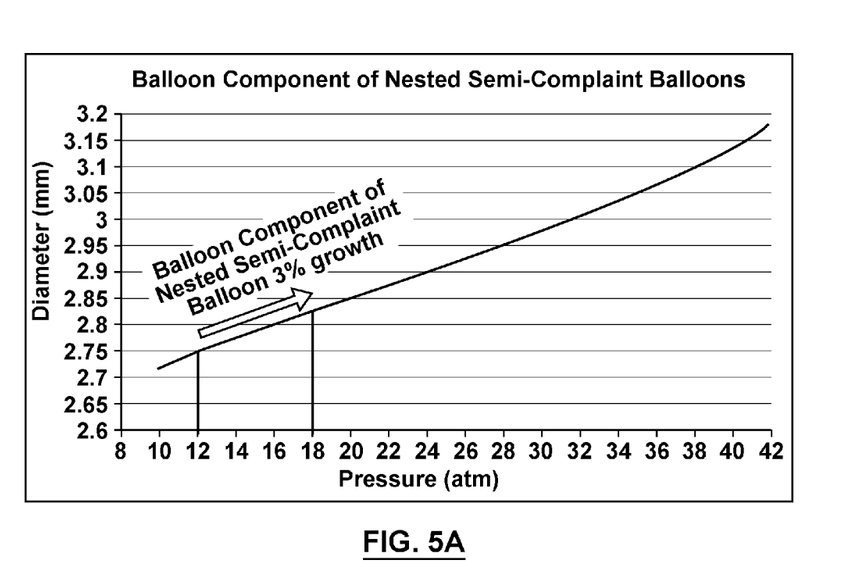
FIG. 5A is a graph that depicts a diameter compliance curve for a balloon component comprised of inner and outer balloons in accordance with embodiments hereof.
Figure 5B:
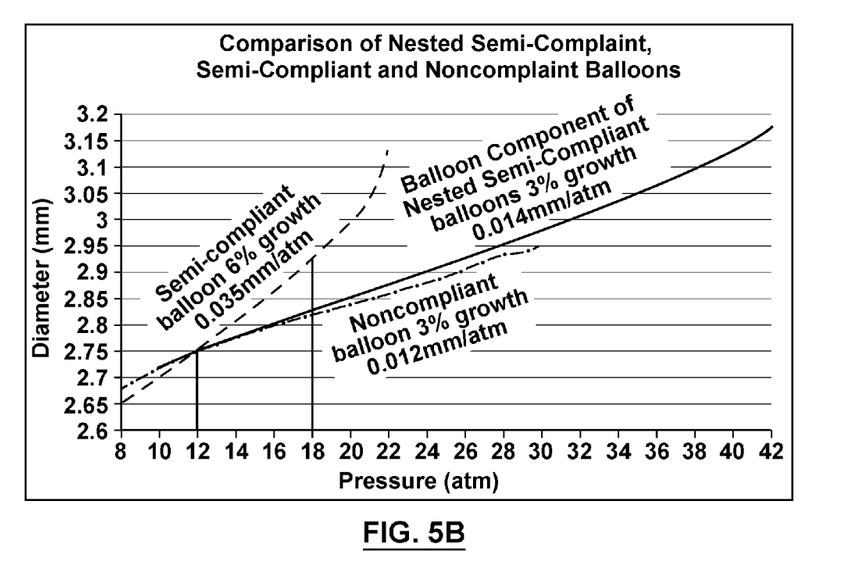
FIG. 5B is a graph that depicts a comparison of the diameter compliance curve of FIG. 5A with the diameter compliance curves of FIGS. 1A and 1B.

Separately or individually the inner and outer balloons 224, 226 exhibit a diameter compliance curve of a semi-compliant balloon, as shown in FIG. 1B, such that if inflated separately each of the inner and outer balloons 224, 226 may individually experience 6% growth in a nominal diameter thereof (or approximately 0.34 mm/Atm between 12 Atm and 18 Atm. However, when the inner and outer balloons 224, 226 are assembled together in a nested arrangement to form the balloon component 108 in accordance with embodiments hereof, the balloon component 108 will have a double wall thickness of approximately 0.0024 inch and will exhibit a diameter compliance curve as shown in FIGS. 5A and 5B that is substantially similar to a diameter compliance curve of a single-wall noncompliant balloon having a double wall thickness of approximately 0.0019 inch, as shown in FIG. 1B and as shown by comparison in FIG. 5B. More particularly, with reference to FIGS. 5A and 5B, the balloon component 108 comprised of nested inner and outer balloons 224, 226 and including a hole 125 has a diameter compliance curve that represents 3% growth in a nominal diameter $D_N$ thereof (or approximately 0.12 mm/Atm) between 12 Atm and 18 Atm, which is substantially similar to a diameter compliance curve of a noncompliant balloon that represents 3% growth in a nominal diameter thereof (or approximately 0.14 mm/Atm) between 12 Atm and 18 Atm.

While the nested balloon component 108 can provide a diameter compliance curve similar to that of a single-wall non-compliant balloon, the burst pressure of balloon component 108 is significantly higher, as illustrated in FIG. 5B. Additionally, the trackability of a catheter mounted with balloon component 108 was shown in animal and bench testing to be better than a comparable catheter equipped with a single-wall non-compliant balloon. Although a single-wall non-compliant balloon could be modified to provide a diameter compliance curve and high burst pressure similar to those features of the nested semi-compliant balloon of FIG. 5B, such a single-wall non-compliant balloon would have seriously compromised deflated profile and trackability because the material of such a balloon would have to be stiffer and/or the balloon wall would have to be thicker. Therefore, the nested balloon component 108 of the invention provides an unusual combination of high burst strength, low diameter compliance, low deflated profile and good trackability.

A method of forming a balloon catheter in accordance with embodiments hereof includes possessing, providing, or obtaining first and second balloons. In an embodiment, each of the first and second balloons may be stretch-blow molded from a respective parison of a polymeric material within a respective mold cavity shaped to form each balloon. Each of the respective mold cavities may be configured to mold identical cylindrical body segments 240, 241 and would have respective end areas for molding the proximal and distal neck and cone segments 232, 234, 236, 238 of the formed inner balloon 224 to be of a slightly smaller outer dimension than the proximal and distal neck and cone segments 233, 235, 237, 239 of the formed outer balloon 226. In this manner the inner and outer balloons 224, 226 may be formed to allow the uninflated inner balloon 224 to be positioned within the outer balloon 226 as described herein. In embodiments hereof and as noted above, the first or inner balloon 224 and the second or outer balloon 226 are formed such that at least cylindrical body segments 240, 241 thereof have the same wall thickness, the same working length and substantially the same nominal inflated diameter.

In embodiments hereof and as noted above, each of the first or inner balloon 224 and the second or outer balloon 226 may be a semi-compliant balloon. Methods and processing steps for forming a semi-compliant dilatation balloon are known to one of skill in the art of medical balloon design and therefore are not detailed herein.

Prior to assembling the first or inner balloon 224 and the second or outer balloon 226, a pinhole is made in the outer balloon 226 in a desired location for the hole 125. In an embodiment, the outer balloon 226 is inflated via an air supply, such as to 6 Atm, and a sharp tool, such as an 0.008 inch diameter needle, is inserted through one of the proximal and distal neck segments 233, 237 to create the hole 125. The insertion depth of the needle may be adjusted to control the final diameter of hole 125, which may be approximately 0.005 inch in an embodiment. Alternatively, hole 125 may be created using a hollow punch or an ablation laser beam. Due to the pressure of the air within the outer balloon 226, when the pinhole is being created very small amounts of material may be pushed outward leaving as clean a cut as possible. In alternate embodiments, the pinhole may be made in one of the tapered proximal and distal cone segments 235, 239 of the inflated outer balloon 226 so as to be located very near the respective juncture 231, 223 and thereby to create the hole 125 therein.

In a method of forming a balloon catheter in accordance herewith, the first or inner balloon 224 and the second or outer balloon 226 are assembled to produce the balloon component 108 by sufficiently folding the inner balloon 224 so that it may be pulled within the outer balloon 226. Thereafter, the proximal neck segments 232, 233 of the inner and outer balloons 224, 226 are coaxially aligned and a distal portion of the outer shaft component 106 is inserted therein. A thermal or melt bond may then be formed to attach the proximal neck segments 232, 233 of the inner and outer balloons 224, 226 to the outer shaft component 106. After the proximal bond is made the interior 229 of the inner balloon 224 is in fluid communication with an inflation lumen 122 of the catheter proximal segment 102 for receiving inflation fluid therefrom. In addition, the proximal bond seals a proximal end of the outer balloon 226 to seal off the interior 227 thereof. In embodiments hereof prior to forming the proximal balloon bond with the outer shaft component 106, the proximalmost ends of the proximal neck segments 232, 233 of the inner and outer balloons 224, 226 may be either longitudinally aligned or in a stepped arrangement, wherein in the stepped arrangement the proximalmost end of the outer balloon 226 may be distally displaced from the proximalmost end of the inner balloon 224.

A method of forming a balloon catheter in accordance herewith may further include coaxially aligning the distal neck segments 236, 237 of the inner and outer balloons 224, 226 with a distal portion of the inner shaft component 114 that is inserted therein. A thermal or melt bond, by any suitable manner described above, is then formed to attach the distal neck segments 236, 237 of the inner and outer balloons 224, 226 to the inner shaft component 114. In embodiments hereof prior to forming the distal balloon bond with the inner shaft component 114, the distalmost ends of the distal neck segments 236, 237 of the inner and outer balloons 224, 226 may be either longitudinally aligned or in a stepped arrangement, wherein in the stepped arrangement the distalmost end of the outer balloon 226 may be proximally displaced from the distalmost end of the inner balloon 224. The distal bond seals distal ends of the inner and outer balloons 224, 226 so as to seal off or close the respective distal ends of the interiors 229, 227 thereof. During formation of the proximal and distal bonds care is taken to assure that no bonding occurs in an area of the pre-formed hole 125, particularly when the hole 125 has been made within one of the proximal and distal neck segments 233, 237 of the outer balloon 226.

In a method of forming a balloon catheter after balloons 224, 226 have been bonded in place, inner balloon 224 may be inflated within outer balloon 226 to a pressure of 35 Atm and held inflated for a period of time, such as for a few seconds. During this initial inflation to the expanded configuration shown in FIG. 3B, substantially all residual air or other fluid that may have been trapped within the interior 227 of the outer balloon 226 is expelled or vented to the ambient environment via the hole 125 as the inner balloon 224 expands to completely fill the interior 227 of outer balloon 226. Thereafter a vacuum may be applied to remove the inflation fluid from the interior 229 of the inner balloon 224, which simultaneously deflates the inner and outer balloons 224, 226 to their uninflated state so that the balloon component 108 may be wrapped about the catheter shaft and heat set in the wrapped configuration to achieve a low profile. In an embodiment, during an initial venting and/or after wrapping and heat setting, substantially all residual air or other fluid may be expelled from the interior 227 of the outer balloon 226 via the hole 125 and due to the extremely small size and positioning of the hole 125 (particularly along one of the proximal and distal neck segments) air or other fluid will not reenter the interior 227 of the outer balloon 226 therethrough.

In accordance with the method described above, the inner balloon 224 is disposed within the interior 227 of the outer balloon 226, and the interior 227 of the outer balloon 226 is not configured to be in fluid communication with the interior 229 of the inner balloon 224, the lumen 122 of the catheter proximal segment 102 or any other source of fluid from the catheter 100.

In embodiments hereof, the outer shaft component 106 and the inner shaft component 114 are tubular structures that may be formed of one or more polymeric materials, non-exhaustive examples of which include polyethylene, polyethylene block amide copolymer (PEBA), polyamide and/or combinations thereof, either laminated, blended or co-extruded. Optionally, the outer shaft component 106 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of the outer shaft component 106 may be formed from a reinforced polymeric tube. Additional catheter components that may be desired for certain functionalities and applications may be added to or utilized with the balloon catheter 100 then those described herein, as would be readily apparent to one of ordinary skill in the art of catheter design without departing from the scope hereof. As well additional processing and finishing steps may be performed on the balloon catheter 100, as would be readily apparent to one of ordinary skill in the art of catheter design without departing from the scope hereof.

Although described in relation to a balloon angioplasty procedure, it should be understood that the methods and apparatus described herein may be used for any medical procedure which utilizes balloon inflation including but not limited to a stenting procedure and/or a graft implantation procedure. Typically, a guiding catheter is first inserted through an incision (not shown) and into a femoral artery of a patient. For example, the Seldinger technique may be utilized for percutaneously introducing the guiding catheter.

Figure 6:
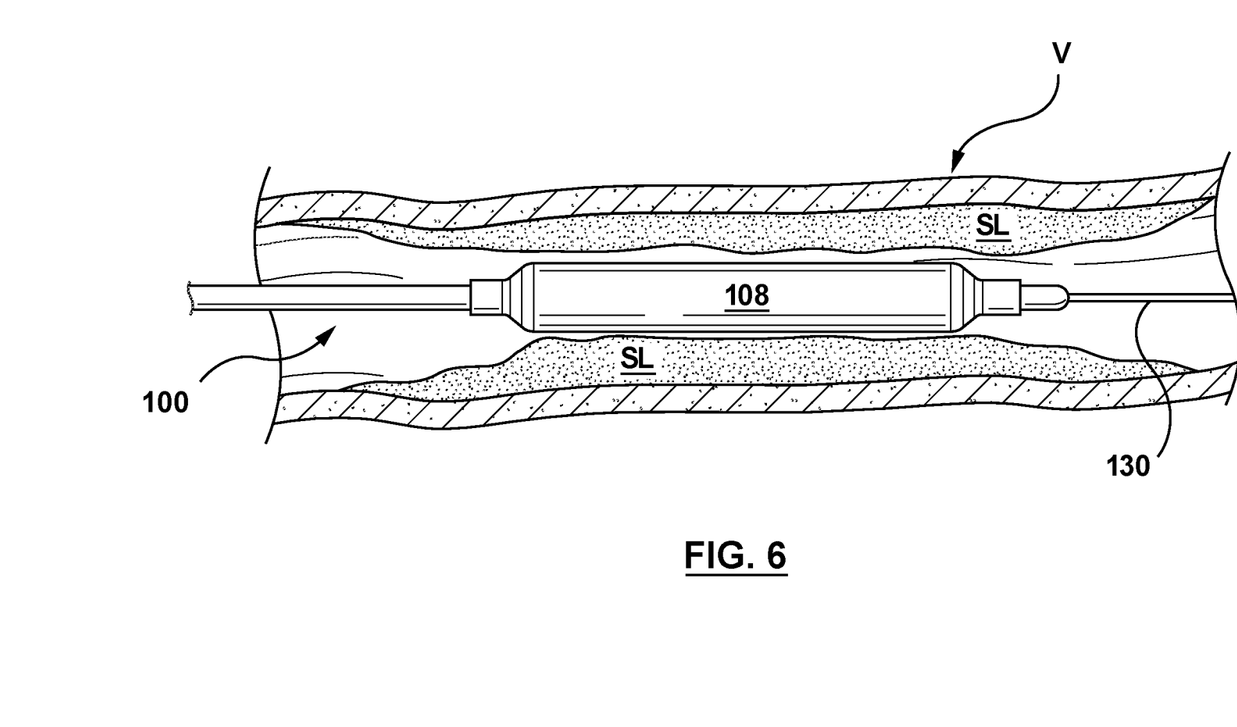
FIG. 6 illustrates a balloon catheter in accordance with an embodiment hereof disposed within a stenotic or heavily calcified lesion.

A guidewire 130 may be introduced and maneuvered through the vasculature to a treatment site, which in this instance is a stenotic or heavily calcified lesion SL within a vessel V as shown in FIG. 6, and the catheter 100 may be subsequently advanced thereover to the treatment site, or alternatively the guidewire 130 and the catheter 100 may have been simultaneously tracked to the stenotic lesion SL. As shown in FIG. 6, the catheter 100 is advanced until the balloon component 108 successfully crosses the stenotic lesson SL to become longitudinally centered therein.

Once the balloon component 108 is disposed within the lesion, inflation fluid is introduced into the inner balloon 224, as discussed above, such that the balloon component 108 begins to radially expand. The balloon component 108 will radially expand to its fully inflated configuration, or nominal diameter $D_N$ shown in FIG. 3B. Balloon component 108 may be pressurized to any suitable pressure including, if necessary, a high pressure, such as 35 Atm, to dilate the stenotic lesion SL and to thereby enlarge the lumen of the vessel V. In an embodiment, the force exerted by the balloon component 108 may radially compress the stenotic lesion SL, or may crack the stenosis and radially stretch the wall of the vessel V, or may impart a combination of both effects. Once the angioplasty procedure is completed, inflation fluid is withdrawn from the inner balloon 224 in order to deflate the balloon component 108 so that it returns to a suitable low profile for removal.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A balloon catheter comprising:
 a high-pressure balloon component including,
 an inner balloon having proximal and distal neck segments, proximal and distal cone segments and a cylindrical body, the inner balloon defining an interior that is in fluid communication with a lumen of the catheter for receiving inflation fluid therefrom, and
 an outer balloon disposed about the inner balloon, the outer balloon having proximal and distal neck segments, proximal and distal cone segments and a cylindrical body, the outer balloon defining an interior within which the inner balloon is disposed, wherein the outer balloon has a hole in a wall thereof for venting the interior of the outer balloon to ambient environment,
 wherein the proximal neck segments of the inner and outer balloons are bonded to an outer shaft component of the catheter, the distal neck segments of the inner and outer balloons are bonded to an inner shaft component of the catheter and the hole in the wall of the outer balloon is formed within a non-bonded area of one of the proximal and distal neck segments of the outer balloon, wherein each of the inner and outer balloons is formed to be a semi-compliant balloon such that each of the inner and outer balloons individually has a diameter compliance curve that is similar to a diameter compliance curve of a semi-compliant balloon, and wherein the balloon component has a diameter compliance curve that is substantially similar to a diameter compliance curve of a noncompliant balloon.

2. The balloon catheter of claim 1, wherein the interior of the outer balloon is not in fluid communication with the interior of the inner balloon, the lumen of the catheter or any other source of fluid from the catheter.

3. The balloon catheter of claim 1, wherein when the balloon component is in an uninflated state the inner balloon and the outer balloon are shaped and sized such that a space is defined therebetween within the interior of the outer balloon.

4. The balloon catheter of claim 3, wherein when the balloon component is in an uninflated state a wall of the inner balloon is wrinkled and when the balloon component is in an inflated state the wall of the inner balloon is smooth and wrinkle-free.

5. The balloon catheter of claim 3, wherein when the inner balloon receives inflation fluid and expands within the interior of the outer balloon any residual air therebetween is expelled through the hole in the wall of the outer balloon.

6. The balloon catheter of claim 5, wherein when the balloon component is in an inflated state the cylindrical body of the inner balloon and the cylindrical body of the outer balloon are in continuous contact with each other.

7. The balloon catheter of claim 6, wherein when the balloon component is in the inflated state the outer balloon constrains further radial expansion of the inner balloon thereby allowing a high pressure to be maintained by the balloon component without bursting.

8. The balloon catheter of claim 7, wherein the high pressure is at least 35 ATM.

9. The balloon catheter of claim 1, wherein the cylindrical body of the inner balloon and the cylindrical body of the outer balloon are formed to have the same wall thickness, the same working length and the same inflated diameter.

10. The balloon catheter of claim 1, wherein the proximal neck segments of the inner and outer balloons are thermally bonded to the outer shaft component and wherein the distal neck segments of the inner and outer balloons are thermally bonded to the inner shaft component.

11. The balloon catheter of claim 1, wherein the hole in the wall of the outer balloon is in the non-bonded area of the proximal neck segment of the outer balloon adjacent the proximal cone segment of the outer balloon.

12. A balloon catheter comprising:

an outer shaft component defining a lumen;

an inner shaft component having at least a proximal portion disposed within the lumen of outer shaft component; and a high-pressure balloon component including, an inner balloon having cylindrical proximal and distal neck segments, tapered proximal and distal cone segments and a cylindrical body, the inner balloon defining an interior that is in fluid communication with a lumen of the catheter for receiving inflation fluid therefrom, and an outer balloon surrounding the inner balloon, the outer balloon having cylindrical proximal and distal neck segments, tapered proximal and distal cone segments and a cylindrical body, the outer balloon defining an interior within which the inner balloon is disposed, wherein the outer balloon has a hole in a wall thereof for venting the interior of the outer balloon to ambient environment, the hole being formed in the wall of the outer balloon in one of the cylindrical proximal neck segment and the cylindrical distal neck segment, wherein the cylindrical proximal neck segments of the inner and outer balloons are bonded to the outer shaft component of the catheter, and the cylindrical distal neck segments of the inner and outer balloons are bonded to the inner shaft component of the catheter.

13. The balloon catheter of claim 12, wherein the hole in the wall of the outer balloon is formed within a non-bonded area of one of the cylindrical proximal and distal neck segments of the outer balloon.

14. The balloon catheter of claim 13, wherein the hole in the wall of the outer balloon is in the non-bonded area of the cylindrical proximal neck segment of the outer balloon to be proximal of a juncture of the outer balloon, wherein the juncture is substantially a demarcation between the cylindrical proximal neck segment and the tapered proximal cone segment of the outer balloon.

15. The balloon catheter of claim 12, wherein each of the inner and outer balloons is formed to be a semi-compliant balloon such that each of the inner and outer balloons individually has a diameter compliance curve that is similar to a diameter compliance curve of a semi-compliant balloon, and wherein the balloon component has a diameter compliance curve that is substantially similar to a diameter compliance curve of a noncompliant balloon.

* * * * *